US009095141B2

(12) United States Patent
Carlson et al.

(10) Patent No.: US 9,095,141 B2
(45) Date of Patent: *Aug. 4, 2015

(54) ANTIFOULING COMPOSITIONS INCLUDING DIOXABORINANES AND USES THEREOF

(71) Applicant: Empire Technology Development LLC, Wilmington, DE (US)

(72) Inventors: William B. Carlson, Seattle, WA (US); Gregory D. Phelan, Cortland, NY (US)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 63 days.

This patent is subject to a terminal disclaimer.

(21) Appl. No.: 13/761,576

(22) Filed: Feb. 7, 2013

(65) Prior Publication Data

US 2014/0037704 A1    Feb. 6, 2014

(51) Int. Cl.
*A01N 55/08*    (2006.01)
*C09D 5/16*    (2006.01)
*C08K 3/00*    (2006.01)
*C08K 3/38*    (2006.01)

(52) U.S. Cl.
CPC ............ *A01N 55/08* (2013.01); *C09D 5/1612* (2013.01); *C08K 3/005* (2013.01); *C08K 3/38* (2013.01)

(58) Field of Classification Search
None
See application file for complete search history.

(56) References Cited

U.S. PATENT DOCUMENTS

| | | | |
|---|---|---|---|
| 3,025,274 A | 3/1962 | Thomas et al. | |
| 3,180,730 A | 4/1965 | Klupfel et al. | |
| 3,234,191 A | 2/1966 | Woods et al. | |
| 3,658,520 A | 4/1972 | Brantly et al. | |
| 4,608,440 A | 8/1986 | Saischek et al. | |
| 4,720,432 A | 1/1988 | VanSlyke et al. | |
| 4,778,833 A | 10/1988 | Van Der Drift et al. | |
| 5,034,296 A | 7/1991 | Ong et al. | |
| 5,055,366 A | 10/1991 | Yu et al. | |
| 5,061,569 A | 10/1991 | VanSlyke et al. | |
| 5,149,609 A | 9/1992 | Yu et al. | |
| 5,521,165 A | 5/1996 | Warren et al. | |
| 5,589,320 A | 12/1996 | Ohnishi et al. | |
| 5,633,236 A | 5/1997 | Warren et al. | |
| 5,759,709 A | 6/1998 | Doi et al. | |
| 5,895,692 A | 4/1999 | Shirasaki et al. | |
| 6,149,927 A | 11/2000 | Ghosh | |
| 6,291,549 B1 | 9/2001 | Mechtel et al. | |
| 6,361,886 B2 | 3/2002 | Shi et al. | |
| 6,365,066 B1 | 4/2002 | Podszun et al. | |
| 6,395,826 B1 | 5/2002 | Mager et al. | |
| 6,462,102 B1 | 10/2002 | Yamamori et al. | |
| 6,465,115 B2 | 10/2002 | Shi et al. | |
| 6,565,996 B2 | 5/2003 | Hatwar et al. | |
| 6,596,415 B2 | 7/2003 | Shi et al. | |
| 6,753,397 B2 | 6/2004 | Nakamura et al. | |
| 6,958,366 B2 | 10/2005 | Tokunaga et al. | |
| 7,125,633 B2 | 10/2006 | Mishra et al. | |
| 8,546,617 B1 | 10/2013 | Carlson et al. | |
| 2004/0106004 A1 | 6/2004 | Li | |
| 2005/0013939 A1 | 1/2005 | Vinden et al. | |
| 2005/0184287 A1 | 8/2005 | Herron et al. | |
| 2005/0233165 A1 | 10/2005 | Ido et al. | |
| 2007/0049778 A1 | 3/2007 | Nomura et al. | |
| 2008/0286566 A1 | 11/2008 | Prakash | |
| 2008/0293848 A1 | 11/2008 | Tomko et al. | |
| 2009/0253879 A1 | 10/2009 | Nishio et al. | |
| 2010/0168851 A1* | 7/2010 | Vanderbilt et al. ........... | 623/6.62 |
| 2010/0190884 A1 | 7/2010 | Gillard et al. | |
| 2010/0222452 A1 | 9/2010 | Kawahara | |
| 2013/0059210 A1* | 3/2013 | Yu et al. ........................ | 429/338 |

FOREIGN PATENT DOCUMENTS

| | | | |
|---|---|---|---|
| GB | 0 901 567 | | 7/1962 |
| JP | 63003051 A | * | 1/1988 |
| JP | 4172456 | | 6/1992 |
| JP | 2006124639 A | | 5/2006 |
| JP | 2006257048 A | | 9/2006 |
| JP | 2006309120 A | | 11/2006 |
| WO | 9505081 A1 | | 2/1995 |
| WO | 03084968 A1 | | 10/2003 |

OTHER PUBLICATIONS

Sigma-Aldrich, "Stabilizers," <http://www.sigmaaldrich.com/materials-science/material-science-products.html?TablePage=20202172>, published Dec. 4, 2008, p. 1-7.*

Tsukahara, Y. et al., "Halogen-Containing Resin Composition Having Excellent Weatherability," Translation of JP 63003051 A, Translated by: Schreiber Translations, Inc., Translated Nov. 2014, p. 1-39.*

Avantor Performance Materials, Material Safety Data Sheet for: Sodium Benzoate, MSDS ID:S2930, Version#: 01, revised Dec. 12, 2011, 6 pages.

Bebernitz, G.R., et al., "Reduction in glucose levels in STZ diabetic rats by 4-(2,2-dimethyl-1-oxopropyl)benzoic acid: a prodrug approach for targeting the liver," Feb. 2001, J Med Chem, vol. 4, No. 4, pp. 512-523.

David, Serge, "The anomalous reactivity of the bis(dibutylstannylene) acetal of pentaerythritol: a case of triple activation," 2001, Carbohyd. Res., vol. 331, pp. 327-329.

International Search Report and Written Opinion of the International Searching Authority for International Application No. PCT/US2012/48996 mailed Oct. 16, 2012 (9 pages).

Kartal, S. Nami et al., "Laboratory evaluation of boron-containing quaternary ammonia compound, didecyl dimethyl ammonium tetrafluoroborate (DBF) for inhibition of mold and stain fungi," (2005), European Journal of Wood and Wood Products, vol. 63, No. 1, pp. 73-77.

(Continued)

Primary Examiner — Tracy Vivlemore
Assistant Examiner — Monica Shin
(74) Attorney, Agent, or Firm — Foley & Lardner LLP

(57) ABSTRACT

An antifouling composition including a compound having a dioxaborinane moiety is provided. Methods of killing, or deterring the growth of, one or more organisms on an article include coating or impregnating the article with the antifouling composition, where the organisms live in fresh water or salt water.

16 Claims, No Drawings

(56) References Cited

OTHER PUBLICATIONS

Meinhold, R. H. "Aromatic boronic acids as wood preservatives, including solid state NMR studies" (1993) Ind. Res. Ltd. Rep. (89), 42 pages.

Miyaura, N., et al., "Stereoselective synthesis of arylated (E)-alkenes by the reaction of alk-1-enylboranes with aryl halides in the presence of palladium catalyst," 1979, J. Chem. Soc., Chem. Commun., Issue 19, pp. 866-867.

Miyaura, Norio et al., "Palladium-Catalyzed Cross-Coupling Reactions of Organoboron Compounds," (1995), Chemical Reviews, vol. 95, No. 7, pp. 2457-2483.

Rose Mill Chemicals & Lubricants, "Material Safety Data Sheet: Borax 5 mol," Revised Apr. 4, 2009, retrieved from http://www.rosemill.com, 2 pages.

Science Lab, "Material Safety Data Sheet: Pentaerythritol MSDS," Updated Jun. 9, 2012, retrieved from: http://www.sciencelab.com/msds.php?msdsId=9926416, 5 pages.

Sigma-Aldrich Co., "Material Safety Data Sheet: Sample Diluent IGM," dated Apr. 26, 2002, 1 page.

Thevenon, Marie-France et al., "High performance tannin resin-boron wood preservatives for outdoor end-uses," European Journal of Wood and Wood Products, (Nov. 2009), vol. 67, No. 1, pp. 89-93.

Aldrich Chemistry "Handbook of Fine Chemicals," Australian/ New Zealand Edition, 2009-2010, pp. 71, 569, 1515, 2079 and 2706.

Biobor Information Sheet, retrieved from http://webcache.googleusercontent.com/search?q=cache:ArtSDCpCY3gJ:www.seriouslostfan.com/topics/Biobor posted on Jul. 27, 2010, pp. 1-2.

Bogdal, D., et al., "Halogenation of carbazole and other aromatic compounds with hydrohalic acids and hydrogen peroxide under microwave irradiation," Green Chem., vol. 6, pp. 110-113 (2004).

Butler, D.N., and Soloway, A. H., "Attempted Synthesis of 2,4-Dihydroxy-4,3-borazaropyridine. Preparation of Aminoalkylboronic Acids," Journal of Medicinal Chemistry, vol. 9, No. 3, pp. 362-365 (May 1966).

Butler, D.N., and Soloway, A. H., "Monohydroboration of N-Alkenylcarbamates; Preparation of Aminoalkylboronic Acids," Chemical Communications, No. 15, p. 333 (1965).

CAS RN 1141927-92-5, STN Entry Date May 3, 2009.
CAS RN 54383-83-4, STN Entry Date Nov. 16, 1984.
CAS RN 84063-31-0, STN Entry Date Nov. 16, 1984.
CAS RN 84063-33-2, STN Entry Date Nov. 16, 1984.
CAS RN 886974-32-9, STN Entry Date Jun. 6, 2006.
CAS RN 914100-80-4, STN Entry Date Nov. 28, 2006.

Dandin, M., et al., "Optical filtering technologies for integrated fluorescence Sensors," Lab Chip, vol. 7, pp. 955-977 (2007).

Findley, T., et al., "Epoxidation of unsaturated fatty materials with peracetic acid in glacial acetic acid solution," J. Am. Chem. Soc., vol. 67, No. 3, pp. 412-414 (1945).

Hwang, J. et al., "Synthesis and characterization of photoconducting non-linear optical polymers containing indole-benzoxazole moiety," Polymer, vol. 42, pp. 3023-3031 (2001).

International Search Report and Written Opinion for international application No. PCT/US2012/031220, mailed on Jul. 6, 2012, pp. 12.

International Search Report and Written Opinion received for PCT/US/2012/030315 mailed Jun. 6, 2012.

Katsuki, K., et al., "Preparation of Carbazole Polymer Thin Films by Electron-Assisted Deposition of 3-(N-Carbazolyl)propyl Acrylate," Jpn. J. Appl. Phys., vol. 44, No. 6A, pp. 4182-4186 (Jun. 10, 2005).

Kimyonok, A., et al., "Norbornene-Based Copolymers with Iridium Complexes and Bis(carbazolyl)fluorene Groups in Their Side-Chains and Their Use in Light-Emitting Diodes," Chem. Mater., vol. 19, No. 23, pp. 5602-5608 (Oct. 16, 2007).

Madani, A., et al. "Experimental study of liquid-crystal alignment on a surface relief grating," Laser Physics, vol. 16, No. 8, pp. 1197-1201 (Aug. 2006).

Mak, C. S. K., and Chan, W. K., "Electroluminescence from Metal-Containing Polymers and Metal Complexes with Functional Ligands", Highly Efficient OLEDs with Phosphorescent Materials, Chapter 10, pp. 329-362 (2008).

Mallinckrodt Baker, Inc., "Material Safety Data Sheet: Sodium Benzoate," accessed at http://web.archive.org/web/20110514220854/http://www.jtbaker.com/msds/englishhtml/s2930.htm, effective Date: Aug. 17, 2009, pp. 1-4.

Matsubara, H., et al., "A New Series of Liquid Crystalline Side-chain Polymers Containing Boron Atoms," Chemistry Letters, vol. 8, pp. 1519-1522 (1989).

Matsubara, H., et al., "Syntheses and Properties of New Liquid-Crystalline Polymers Having 1,3,2-Dioxaborinane Pendants," Bulletin of the Chemical Society of Japan, vol. 66, No. 2, pp. 578-584 (1993).

Mulvaney, J.E., et al., "Preparation of Vinyl Boronate Copolymers and Reactions," Journal of Polymer Science: Polymer Chemistry Edition, vol. 20, Issue 7, pp. 1949-1952 (Jul. 1982).

Murata, M., et al., "Synthesis of benzylboronates via palladium catalyzed borylation of benzyl halides with pinacolborane," Synthetic Commun, vol. 32, No. 16, pp. 2513-2517 (2002).

Pesticide Products, "Timbertreat b wood preservative booster," Biobor jf, PAN Pesticides Database, accessed at http://www.pesticideinfo.org/Detail_Product.jsp?REG_NR=06521700001&DIST_NR=060061, accessed on Sep. 26, 2014, pp. 1-3.

Pietsch, C., et al., "PMMA based soluble polymeric temperature sensors based on UCST transition and solvatochromic dyes", Polymer Chemistry, vol. 1, Issue 7, pp. 1005-1008, (2010).

Rasset-Deloge, C., et al., "ChemInform: Synthesis of Vinylboronates β-Substituted by an Electron-Withdrawing Group: A New Class of Electron-Poor Olefins," ChemInform, vol. 24, No. 2, pp. 285-290 (Jan. 12, 1993).

Schunicht, C., et al., "ChemInform: Microgel-Supported Oxazaborolidines: Novel Catalysts for Enantioselective Reductions," ChemInform, vol. 56, No. 12, pp. 1693-1699 (Jun. 27, 2000).

Shirota, Y., et al., "Charge Carrier Transporting Molecular Materials and Their Applications in Devices," Chemical Reviews, vol. 107, No. 4, pp. 953-1010 (Apr. 11, 2007).

Suzuki, A., "Recent advances in the cross-coupling reactions of organoboron derivatives with organic electrophiles," Journal of Organometallic Chemistry, vol. 576, Issues 1-2, pp. 147-168, (Mar. 15, 1999).

Voloshin, Y.Z. et al., "Application of the allylboration reaction of terminal acetylenes with allyldihaloboranes for the preparation of capping agents for the synthesis of precursors of polymeric iron(II) clathrochelates," Russian Chemical Bulletin, vol. 55, No. 11, pp. 1971-1981 (Nov. 2006).

Wulff, G., et al., "Enzyme-Analogue Built Polymers, 23. Influence of the Structure of the Binding Sites on the Selectivity for Racemic Resolution," Die Makromol. Chem., vol. 188, No. 4, pp. 741-748 (Apr. 1987).

Wulff, G., et al., "Über enzymanalog gebaute polymer, 16. Über den Einfluβ der flexibilitat der haftgruppen auf die racemattrennungsfähigkeit," Die Makromolekulare Chemie, vol. 183, No. 10, pp. 2469-2477 (Oct. 18, 1982).

Wulff, G., et al., "Über enzymanalog gebaute Polymere, III. Zur Synthese von polymerisierbaren D-Glycerinsaurederivaten," Chemische Berichte, vol. 107, No. 10, pp. 3364-3376 (Oct. 1974).

Yalinkilic, M.K., et al., "Enhancement of the biological resistance of wood by phenylboronic acid treatment," Journal of Wood Science, vol. 44, Issue 2, pp. 152-157 (Apr. 1998).

Yang, C., et al., "Alkylboronic Esters from Copper-Catalyzed Borylation of Primary and Secondary Alkyl Halides and Pseudohalides," Angewandte Chemie International Edition, vol. 51, No. 2, pp. 528-532 (Jan. 9, 2012).

International Search Report and Written Opinion for Intl. Pat. Appln. No. PCT/US2012/031220, mailed on Jul. 6, 2012.

Kartal, S. Nami al., "Laboratory evaluation of boron-containing quaternary ammonia compound, didecyl dimethyl ammonium tetrafluoroborate (DBF) for control of decay and termite attack and fungal staining of wood," (2006) European Journal of Wood and Wood Products, vol. 64, No. 1, pp. 62-67.

Non-Final Office Action for U.S. Appl. No. 13/554,783, mailed on Mar. 26, 2013.

(56) References Cited

OTHER PUBLICATIONS

Notice of Allowance for U.S. Appl. No. 13/554,783, mailed on Jun. 13, 2013.

"Sigma-Aldrich," (2008) accessed at https://web.archive.org/web/20090113184900/http://www.sigmaaldrich.com/materials-science/material-science-products.html?TablePage=20202172, accessed on Feb. 4, 2015, 6 pages.

* cited by examiner

ANTIFOULING COMPOSITIONS INCLUDING DIOXABORINANES AND USES THEREOF

CROSS-REFERENCE TO RELATED APPLICATIONS

This application claims the benefit of priority to International Application No. PCT/US2012/048996, filed on Jul. 31, 2012, which is incorporated herein by reference in its entirety for any and all purposes.

FIELD

The present technology relates to antifouling compositions having compounds including one or more dioxaborinane moieties for use as antifouling agents.

BACKGROUND

The following description is provided to assist the understanding of the reader. None of the information provided or references cited is admitted to be prior art to the present technology.

Once immersed in an aquatic environments, most objects become suitable substrates for the growth of biofilms and/or barnacles. Ships, for example, need to be protected from the growth of biofilms and/or barnacles by the use of antifouling coatings. Antifouling coatings on hulls serve multiple functions, for example, by protecting the hull from the corrosive effects of salt water, preventing life from growing on the hull, and (if pigmented) imparting color to the hull.

Antifouling coatings can reduce energy costs for ships. Hulls are designed to move through water with the least amount of resistance, and burn the least amount of fuel, while maximizing the carrying capacity of the ship. Hull design has advanced considerably over the last century. However, advancements in hull design can be at least partially negated by biofilm and/or barnacle growth on the hull. For example, biofilms can increase drag about 20 percent and barnacles can increase drag about 60 percent. The increased drag on a ship's hull, caused by bioaccumulation, increases fuel consumption. Further, the ship must be periodically taken into a dry dock where the hull can be cleaned at considerable expense. Existing antifouling coatings generally include metals such as tin (e.g., tri-n-butyl tin), copper, or arsenic. While effective, these metal-based antifouling coatings are toxic and damaging to the environment. Improved antifouling coatings are needed that inhibit the growth of biofilms and/or barnacles without substantially harming the environment.

SUMMARY

The present technology provides for antifouling compositions including one or more dioxaborinane moieties that deter or kill organisms that grow in an aqueous environment. The antifouling compositions are environmentally friendly and can be applied to an article and polymerized to effectively fix the dioxaborinane moiety to the article, and minimize or prevent leaching of the dioxaborinane moiety from the article. Articles that are coated or impregnated with the antifouling compositions can be partially or fully submerged in an aqueous environment. Such coated or impregnated articles will deter the growth of organisms.

In accordance with one aspect, an antifouling composition is provided, where the antifouling composition includes a first monomer represented by Formula I:

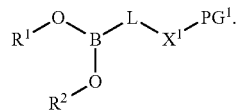

In Formula I, L is absent, alkylenyl, alkenylenyl, or arylene, where the alkylenyl and alkenylenyl are optionally interrupted with one or more oxygen or sulfur atoms; $X^1$ is absent, or is amino, oxo, thio, or phosphino; $PG^1$ is a polymerizable group; $R^1$ and $R^2$ are independently H, alkyl, alkenyl, aryl, $C(O)R^3$, $C(O)OR^3$, $C(O)NHR^3$, or $R^1$ and $R^2$ together with the oxygen atoms to which they are bonded join to form a 5- or 6-membered ring; $R^3$ is H, alkyl, alkenyl, or aryl, where the alkyl and alkenyl are optionally interrupted with one or more oxygen or sulfur atoms. In Formula I, where L and $X^1$ are both absent, and $R^1$ and $R^2$ form a 5- or 6-membered ring, then $PG^1$ is not a vinyl group. The composition may further include a carrier, a resin, a stabilizer, a corrosion inhibitor, or a combination of any two or more thereof.

In accordance with another aspect, an article is provided, where the article contacts an aqueous environment and the article is coated or impregnated with an antifouling composition including one or more dioxaborinane moieties as described herein.

In accordance with yet another aspect, a method of killing, or at least deterring the growth of, one or more organisms on an article, where the organisms live in fresh water or salt water, where the method includes contacting the article with an antifouling composition having a compound comprising one or more dioxaborinane moieties as described herein.

The foregoing summary is illustrative only and is not intended to be in any way limiting. In addition to the illustrative aspects, embodiments and features described above, further aspects, embodiments and features will become apparent by reference to the following detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a monomer" includes a plurality of monomers, and a reference to "an article" is a reference to one or more articles.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, the alkyl groups may be substituted alkyl groups.

Heteroalkyl groups include alkyl groups, as defined herein, substituted by one or more O, N, or S atoms.

Cycloalkyl groups are cyclic alkyl groups having from 3 to 10 carbon atoms. In some embodiments, the cycloalkyl group has 3 to 7 ring members, whereas in other embodiments the number of ring carbon atoms range from 3 to 5, 3 to 6, or 5, 6 or 7. Cycloalkyl groups further include monocyclic, bicyclic and polycyclic ring systems. Monocyclic groups include, e.g., cyclopropyl, cyclobutyl, cyclopentyl, cyclohexyl, and cycloheptyl groups. Bicyclic and polycyclic cycloalkyl groups include bridged or fused rings, such as, but not limited to, bicyclo[3.2.1]octane, decalinyl, and the like. Cycloalkyl groups include rings that are substituted with straight or branched chain alkyl groups as defined above. In some embodiments, the cycloalkyl groups are substituted cycloalkyl groups. Representative substituted alkenyl groups may be mono-substituted or substituted more than once, such as, but not limited to, mono-, di- or tri-substituted with substituents such as those listed above. Representative substituted alkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have from 2 to 24 carbon atoms, and typically from 2 to 10 carbons or, in some embodiments, from 2 to 8, 2 to 6, or 2 to 4 carbon atoms. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

The terms "alkylene," "cycloalkylene," "alkenylene," and "heteroalkylene," "heteroarylene," alone or as part of another substituent means a divalent radical derived from an alkyl, cycloalkyl, alkenyl, heteroalkyl, or heteroaryl group, respectively, as exemplified by —CH$_2$CH$_2$CH$_2$CH$_2$—. For alkylene, cycloalkylene, alkenylene, heteroalkylene, or heteroarylene linking groups, no orientation of the linking group is implied.

The term "amine" (or "amino") as used herein refers to —NHR and —NRR' groups, where R, and R' are independently hydrogen, or a substituted or unsubstituted alkyl, alkenyl, alkynyl, cycloalkyl, aryl or aralkyl group as defined herein. Examples of amino groups include —NH$_2$, methylamino, dimethylamino, ethylamino, diethylamino, propylamino, isopropylamino, phenylamino, benzylamino, and the like.

The term "oxo" refers to a divalent oxygen group. While the term includes doubly bonded oxygen, such as that found in a carbonyl group, as used herein, the term oxo explicitly includes singly bonded oxygen of the form —O— which is part of a polymer backbone. Thus, an oxo group may be part of an ether linkage (—O—), an ester linkage (—O—C(O)—), a carbonate linkage (—O—C(O)O—), a carbamate linkage (—O—C(O)NH— or —O—C(O)NR—), and the like.

"Substituted" refers to a chemical group as described herein that further includes one or more substituents, such as lower alkyl (including substituted lower alkyl such as haloalkyl, hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl), cycloheteroalkyls and the like. These groups may be attached to any carbon or substituent of the alkyl, alkenyl, alkynyl, aryl, cycloheteroalkyl, alkylene, alkenylene, alkynylene, arylene, hetero moieties. Additionally, the substituents may be pendent from, or integral to, the carbon chain itself.

The present technology provides for antifouling compositions having a compound comprising dioxaborinane moieties that kills or deters the growth of organisms that live in fresh water or salt water.

In accordance with one aspect, an antifouling composition is provided, where the antifouling composition includes a first monomer represented by Formula I:

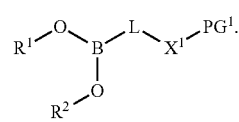

In Formula I, L is absent, alkylenyl, alkenylenyl, or arylene, where the alkylenyl and alkenylenyl are optionally interrupted with one or more oxygen or sulfur atoms; $X^1$ is absent, or is amino, oxo, thio, or phosphino; $PG^1$ is a polymerizable group; $R^1$ and $R^2$ are independently H, alkyl, alkenyl, aryl, C(O)$R^3$, C(O)O$R^3$, C(O)NH$R^3$, or $R^1$ and $R^2$ together with the oxygen atoms to which they are bonded join to form a 5- or 6-membered ring; $R^3$ is H, alkyl, alkenyl, or aryl, where the alkyl and alkenyl are optionally interrupted with one or more oxygen or sulfur atoms. In some embodiments of the first monomer, if L and $X^1$ are both absent, and $R^1$ and $R^2$ form a 5- or 6-membered ring, then $PG^1$ is not a vinyl group. The antifouling composition may further include a carrier, a resin, a stabilizer, a corrosion inhibitor, or a combination of any two or more thereof.

Illustrative groups for $PG^1$ include acrylyl, methacrylyl, epoxyl, isocycanyl, styrenyl, vinyl, oxyvinyl, thiovinyl, ketovinyl, ketoalkyl, ketoalkoxy, ketoaryl, or cycloalkenyl. In other embodiments, $PG^1$ is C(O)C($R^{10}$)═CH$_2$, C(O)CH═CH$_2$, O—CH═CH$_2$, S—CH═CH$_2$, N═C═O,

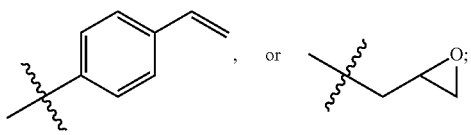

and $R^{10}$ is a $C_1$-$C_8$ alkyl. In some embodiments, $PG^1$ is C(O)C($R^{10}$)═CH$_2$ and $R^{10}$ is H; $C_1$-$C_8$ alkyl, aryl, or CN. In other embodiments, $PG^1$ is —C(O)CH═CH$_2$.

Illustrative groups for $X^1$ are —NH—, —O—, —S—, or —PH—.

In other embodiments, L is $C_1$-$C_{10}$ alkylene, $C_1$-$C_{10}$ heteroalkylene, arylene, or heteroarylene.

In some embodiments, $R^1$ is H and $R^2$ is H; or $R^1$ is $C_1$-$C_6$ alkyl and $R^2$ is $C_1$-$C_6$ alkyl. In other embodiments, $R^1$ and $R^2$ together with the oxygen atoms to which they are bonded join to form a group of formula:

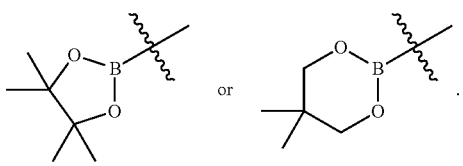

In some embodiments, the antifouling composition includes a first monomer represented by Formula IA:

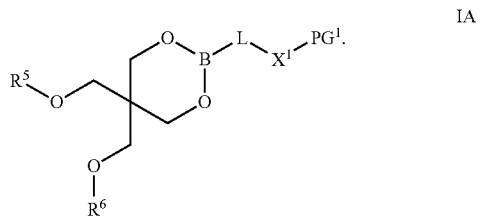

In Formula IA, $R^5$ and $R^6$ are independently H, alkyl, alkenyl, aryl, or —C(O)$R^7$; and $R^7$ is alkyl, alkenyl, or aryl. In other embodiments, $R^5$ is —C(O)alkyl and $R^6$ is —C(O)alkyl. In some embodiments, L is $C_1$-$C_{10}$ alkyl. In other embodiments, $X^1$ is —O—.

On a weight to weight percent basis, the antifouling composition may include a first monomer represented by Formula I or Formula IA in an amount of about 0.1 wt % to 100.0 wt %. In some embodiments, the antifouling composition may include a first monomer represented by Formula I or Formula IA in an amount of about 1.0 wt % to about 10.0 wt %. In some embodiments, the antifouling composition may include a first monomer represented by Formula I or Formula IA in an amount of about 10.0 wt % to about 20.0 wt %. In some embodiments, the antifouling composition may include a first monomer represented by Formula I or Formula IA in an amount of about 20.0 wt % to about 40.0 wt %. In some embodiments, the antifouling composition may include a first monomer represented by Formula I or Formula IA in an amount of about 40.0 wt % to about 60.0 wt %. In some embodiments, the antifouling composition may include a first monomer represented by Formula I or Formula IA in an amount of about 60.0 wt % to about 80.0 wt %. In some embodiments, the antifouling composition may include a first monomer represented by Formula I or Formula IA in an amount of about 80.0 wt % to about 100.0 wt %.

The first monomer, represented by Formula I or Formula IA, may be co-polymerized with a second monomer, for example, to adjust polymer properties for the antifouling composition. A second monomer such as lauryl methacrylate, for example, may be used to lower the glass transition temperature and render the resulting polymer more flexible and stretchable. Alternatively, polymerization of the first monomer, represented by Formula I or Formula IA, with a second monomer such as adamantyl methacrylate, for example, may be used increase the glass transition temperature and render the resulting polymer harder and more glass-like. Other second monomers may be co-polymerized with the first monomer, represented by Formula I or Formula IA, having a dioxaborinane moiety, to add additional features, such as crosslinking capabilities. Illustrative second monomers include methyl methacrylate, butyl acrylate, styrene, alpha-methyl styrene, vinyl acetate, methyl vinyl ketone, ethylene, vinylidene fluoride, vinylidene chloride, vinyl chloride, vinyl fluoride, methyl vinyl ether, tetrafluoroethylene, vinyl pyridine, maleic anhydride, trifluoroethyl methacrylate, vinylcarbazole, vinyl acrylate, glycidyl methacrylate, 4-vinylbenzoic acid, styrene sulfonic acid, ethylene glycol dimethacrylate, divinyl benzene, bis(octyl)itaconate, itaconic acid, and combinations thereof.

Polymerization of the first monomer, or the first and second monomer, may be achieved upon activation of the polymerizable group of the first and/or second monomer. For example, activating of the polymerizable group may include heating the polymerizable group, applying ultraviolet irradiation to the polymerizable group, adding a thermal initiator to the polymerizable group, or adding a photochemical initiator to the polymerizable group. Where activating the polymerizable group includes adding a thermal initiator to the polymerizable group, the thermal initiator may include, but is not limited to, 4,4-azobis(4-cyanovaleric acid), 1,1'-azobis(cyclohexanecarbonitrile), 2,2'-azobisisobutyronitrile, benzoyl peroxide, tert-butyl peracetate, lauroyl peroxide, or dicumyl peroxide. Where activating the polymerizable group includes adding a photochemical initiator to the polymerizable group, the initiator may include, but is not limited to, 3-butyl-2-[5-(1-butyl-3,3-dimethyl-1,3-dihydro-indol-2-ylidene)-penta-1,3-dienyl]-1,1-dimethyl-1H-benzo[e]indolium triphenylbutylborate, 3-butyl-2-[5-(3-butyl-1,1-dimethyl-1,3-dihydro-benzo[e]indol-2-ylidene)-penta-1,3-dienyl]-1,1-dimethyl-1H-benzo[e]indolium triphenylbutylborate, or 6-hydroxy-2,4,5,7-tetraiodo-3-oxo-9,9a-dihydro-3H-xanthene-9-carbonitrile. In some embodiments, activating the polymerizable group includes heating the polymerizable group to a temperature of about 40° C. to about 120° C.

According to another embodiment, an antifouling composition is provided, where the antifouling composition further includes a polymerization product of the first monomer represented by Formula I, and a second monomer. The second monomer may include a polymerizable group $PG^2$, which is configured to polymerize with $PG^1$. The antifouling composition may include about 0.1 wt % to 25 wt % of the polymerization product of the first monomer. In some embodiments, the second monomer is an acrylate or a methacrylate. In other embodiments, the second monomer is represented by Formula II:

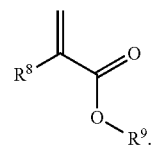

In Formula II, $R^8$ is H; CN; $CF_3$; $CH_3$; or phenyl; and $R^9$ is H; $C_1$-$C_{22}$ alkyl; aryl; or a metal ion. In some embodiments, the metal ion is $Na^+$, $Li^+$, or $K^+$.

In some embodiments, the polymerization product of the first monomer, or the first and second monomer, has a weight average molecular weight of about 5,000 g/mol to about 2,000,000 g/mol. For example, the polymerization product of the first monomer, or the first and second monomer, may have a weight average molecular weight of about 100,000 to about 1,000,000 g/mol.

As noted, the first monomer, represented by Formula I or Formula IA, may be co-polymerized with a second monomer. In some embodiments, the co-polymer is of Formula III:

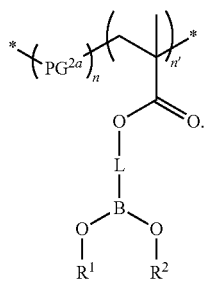

In Formula III, $PG^{2a}$ is the polymerization product of the first monomer and polymerization group $PG^2$; L is an alkylene or arylene group; and n and n' represent the repeat units of the co-polymer.

As noted, the antifouling compositions described herein further include one or more carriers, resins, stabilizers, corrosion inhibitors, or a combination of any two or more thereof. On a weight to weight percent basis, the antifouling composition may include one or more carriers, resins, stabilizers, corrosion inhibitors, or a combination of any two or more thereof in a combined amount of about 0.1 wt % to 99.0 wt %. This may include from about 1.0 wt % to about 10.0 wt %, or from about 10.0 wt % to about 20.0 wt %, or from about 20.0 wt % to about 40.0 wt %, or from about 40.0 wt % to about 60.0 wt %, or from about 60.0 wt % to about 80.0 wt %, or from about 80.0 wt % to about 99.0 wt %, and ranges between any two of these values.

Where the antifouling composition may include one or more carriers, the carrier may be water, alcohol, a glycol-based solvent (e.g., glycol ether), a water repellent, a wax, a hydrogel, a polysaccharide, a hydrocarbon, a petroleum fraction, or a combination of any two or more thereof. On a weight to weight percent basis, the antifouling composition may include one or more carriers in an amount of about 0.1 wt % to 99.0 wt %. This may include from about 1.0 wt % to about 10.0 wt %, or from about 10.0 wt % to about 20.0 wt %, or from about 20.0 wt % to about 40.0 wt %, or from about 40.0 wt % to about 60.0 wt %, or from about 60.0 wt % to about 80.0 wt %, or from about 80.0 wt % to about 99.0 wt %, and ranges between any two of these values.

The antifouling composition may include one or more binders. In some embodiments, the binder is a chlorinated rubber resin, a chlorinated polypropylene resin, a petroleum resin, a alkyl resin, a acrylic resin, a phenolic resin, a synthetic rubber, a epoxy resin, a silicone rubber, a silicon resin, a rosin resin, or a combination of any two or more thereof. On a weight to weight percent basis, the antifouling composition may include one or more binders in an amount of about 0.1 wt % to 99.0 wt %. This may include from about 1.0 wt % to about 10.0 wt %, or from about 10.0 wt % to about 20.0 wt %, or from about 20.0 wt % to about 40.0 wt %, or from about 40.0 wt % to about 60.0 wt %, or from about 60.0 wt % to about 80.0 wt %, or from about 80.0 wt % to about 99.0 wt %, and ranges between any two of these values.

The antifouling composition may include one or more corrosion inhibitors. The corrosion inhibitor may include a cathodic inhibitor or an anodic inhibitor. In some embodiments, the corrosion inhibitor is zinc phosphate. In other embodiments, the corrosion inhibitor is tannic acid, or a derivative thereof, a zinc salt of an amino compound (e.g., an Alcophor® inhibitor such as Alcophor 827, BASF, Ludwigshafen, Germany). Other corrosion inhibitors include, but are not limited to, phosphate esters, imidazolines, benzyltrialkyl ammonium halides, or a combination of any two or more thereof. On a weight to weight percent basis, the antifouling composition may include one or more binders in an amount of about 0.1 wt % to 99.0 wt %. This may include from about 1.0 wt % to about 10.0 wt %, or from about 10.0 wt % to about 20.0 wt %, or from about 20.0 wt % to about 40.0 wt %, or from about 40.0 wt % to about 60.0 wt %, or from about 60.0 wt % to about 80.0 wt %, or from about 80.0 wt % to about 99.0 wt %, and ranges between any two of these values.

The antifouling composition may include one or more stabilizers. In some embodiments, the one or more stabilizers include an antioxidant, a UV absorber, a heat stabilizer, a light stabilizer, or a combination of any two or more thereof. On a weight to weight percent basis, the antifouling composition may include one or more stabilizers in an amount of about 0.1 wt % to 99.0 wt %. This may include from about 1.0 wt % to about 10.0 wt %, or from about 10.0 wt % to about 20.0 wt %, or from about 20.0 wt % to about 40.0 wt %, or from about 40.0 wt % to about 60.0 wt %, or from about 60.0 wt % to about 80.0 wt %, or from about 80.0 wt % to about 99.0 wt %, and ranges between any two of these values.

Illustrative antioxidants include 2,6-di-tert-butyl-4-(4,6-bis(octylthio)-1,3,5-triazin-2-ylamino)phenol, N,N'-di-2-butyl-1,4-phenylene-diamine, stearyl-3-(3',5'-di-tert-butyl-4-hydroxyphenyl)propionate, dioctadecyl 3,3'-thiodipropionate, and combinations of any two or more such antioxidants. Illustrative UV absorbers include 2-benzotriazol-2-yl-4,6-bis-(1,1-dimethyl-propyl)-phenol, 2-(4,6-diphenyl-[1,3,5]triazin-2-yl)-phenol, (2-hydroxy-4-octyloxy-phenyl)-phenyl-methanone, and combinations of any two or more such UV absorbers. Illustrative light stabilizers include hindered amines such as 2,2,6,6-tetramethyl piperidine, bis(1,2,2,6,6-pentamethyl-4-piperidinyl)sebacate, poly[[6-[(1,1,3,3-tetramethylbutyl)amino]-s-triazine-2,4-diyl][2,2,6,6-tetramethyl-4-piperidyl)imino]]hexamethylylene[(2,2,6,6-tetramethyl-4-piperidyl)imino]], and combinations of any two or more such light stabilizers. Illustrative heat stabilizers include butyl tin carboxylate, barium zinc, tris(2,4-ditert-butylphenyl)phosphate, and combinations of any two or more such heat stabilizers.

In some embodiments, the antifouling composition is a coating, such as, for example, a sealant or paint that includes one or more colorants.

In accordance with another aspect, an article is provided, where the article contacts an aqueous environment and the article is coated or impregnated with an antifouling composition, where the antifouling composition includes a first monomer represented by Formula I:

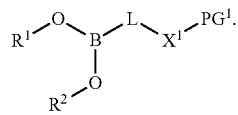

In Formula I: L is absent, alkylenyl, alkenylenyl, or arylene, where the alkylenyl and alkenylenyl are optionally interrupted with one or more oxygen or sulfur atoms; $X^1$ is absent, or is amino, oxo, thio, or phosphino; $PG^1$ is a polymerizable group; $R^1$ and $R^2$ are independently H, alkyl, alkenyl, aryl, $C(O)R^3$, $C(O)OR^3$, $C(O)NHR^3$, or $R^1$ and $R^2$ together with the oxygen atoms to which they are bonded join to form a 5- or 6-membered ring; $R^3$ is H, alkyl, alkenyl, or aryl, where the alkyl and alkenyl are optionally interrupted with one or more oxygen or sulfur atoms. In Formula I, where L and $X^1$ are both absent, and $R^1$ and $R^2$ form a 5- or 6-membered ring, then $PG^1$ is not a vinyl group. The antifouling composition may also include a carrier, a resin, a stabilizer, a corrosion inhibitor, or a combination of any two or more thereof.

The article may be coated or impregnated with an antifouling composition that includes a polymerization product of the first monomer represented by Formula I, and a second monomer, where the second monomer includes a polymerizable group $PG^2$, which is configured to polymerize with $PG^1$. In some embodiments, the second monomer is an acrylate or a methacrylate.

In some embodiments, the article includes steel, concrete, or a polymer. For example, the article may be a hull of a ship, a buoy, a fishing net, a pipeline, a tunnel, a dome, a mine, an aquarium, a bridge, a pier, a dock, a component of a port facility, a component of an electric power station, or a component of an oil producing facility.

Alternatively, the antifouling composition may be used to coat articles having medical applications. For example, in some embodiments, the article is an implanted medical device such as, for example, a stent, an orthopedic prosthesis, a cosmetic implant, a artificial heart valve, or a artificial vascular graft.

As noted above, the article is coated or impregnated with an antifouling composition as described herein, where the article may be coated or impregnated with the antifouling composition under a pressure regime to infuse the antifouling composition into the article (e.g., concrete). The infusion of an antifouling composition, as described herein, into an article may optionally further include the selective application of increased pressure or vacuum.

The articles may be coated or impregnated with an antifouling composition that further includes one or more carriers, resins, stabilizers, corrosion inhibitors, or a combination of any two or more thereof. One or more of the carriers, resins, stabilizers, or corrosion inhibitors may be applied to the article prior to the antifouling composition. One or more of the carriers, resins, stabilizers, or corrosion inhibitors may be applied to the article after the antifouling composition as described herein. In certain embodiments, one or more of these carriers, resins, stabilizers, or corrosion inhibitors may be applied to the article simultaneously with the antifouling composition as described herein.

The polymerization of the monomers within the antifouling composition prevents, or at least minimizes, leaching of the pendant dioxaborinane moiety from the monomer of Formula I, from the article. In certain embodiments, the article has a polymerized solid surface coat of the antifouling composition comprising one or more dioxaborinane moieties.

Polymerization of the monomers within the antifouling composition may be promoted by conventional means. In certain embodiments, the polymerization includes activating the polymerizable group. In other embodiments, activating the polymerizable group includes heating, activating the polymerizable group with electromagnetic radiation, adding a thermal initiator, or adding a photochemical initiator. Electromagnetic radiation includes radiation from the electromagnetic spectrum having a wavelength from 0.1 angstrom (Å) to 1,000 meters (m). In certain embodiments, activating the polymerizable group includes activating the polymerizable group with ultraviolet (UV), visible, or near-infrared (IR) radiation. UV radiation has a wavelength from about 10 nm to about 390 nm. Visible radiation has a wavelength from about 390 nm to about 750 nm. Near-IR radiation has a wavelength from about 750 nm to about 3 μm. In certain embodiments, polymerization of the compound of Formula I is promoted through the application of UV radiation. In certain embodiments, polymerization of the compound of Formula I is promoted by adding a photochemical initiator. In certain embodiments, the polymerization is promoted through the application of heat. In certain embodiments, the polymerization is promoted by adding a thermal initiator.

In accordance with another aspect, a method is provided of killing, or at least deterring the growth of, one or more organisms on an article. Such organisms may be those that grow and propagate in fresh water or salt water. The method may include contacting the article with an antifouling composition including a polymer, where the polymer includes a first monomer represented by Formula I:

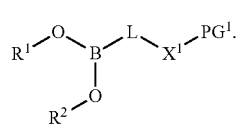

In Formula I, L is absent, alkylenyl, alkenylenyl, or arylene, where the alkylenyl and alkenylenyl are optionally interrupted with one or more oxygen or sulfur atoms; $X^1$ is absent, or is amino, oxo, thio, or phosphino; $PG^1$ is a polymerizable group; $R^1$ and $R^2$ are independently H, alkyl, alkenyl, aryl, $C(O)R^3$, $C(O)OR^3$, $C(O)NHR^3$, or $R^1$ and $R^2$ together with the oxygen atoms to which they are bonded join to form a 5- or 6-membered ring; $R^3$ is H, alkyl, alkenyl, or aryl, where the alkyl and alkenyl are optionally interrupted with one or more oxygen or sulfur atoms. In Formula I, where L and $X^1$ are both absent, and $R^1$ and $R^2$ form a 5- or 6-membered ring, then $PG^1$ is not a vinyl group. The composition may further include a carrier, a resin, a stabilizer, a corrosion inhibitor, or a combination of any two or more thereof. The method may further include exposing the article to an aqueous environment.

In some embodiments, the polymer is a polymerization product of the first monomer represented by Formula I, and a second monomer, where the second monomer includes a polymerizable group $PG^2$, which is configured to polymerize with $PG^1$. In some embodiments, the second monomer is an acrylate or a methacrylate.

The antifouling composition including a polymer, where the polymer includes a first monomer represented by Formula I, may be applied to the article by dipping, soaking, spraying (e.g., spray painting), brushing, rolling, injecting, or any other commonly used methods. The article may be exposed to or at least partially immersed in an aqueous environment, such as fresh water or salt water. An article, such as the hull of a boat, may be in fresh water or salt water. An article, such as a pier, may partially be submerged in fresh water or salt water. The antifouling composition including a polymer, where the polymer includes a first monomer represented by Formula I, may be applied at ambient temperature, or heated to assist the adhesion or penetration of the antifouling composition into or onto the article. In certain embodiments, methods are provided in which the antifouling composition including a polymer which includes a first monomer represented by Formula I, is applied to the article by impregnating it into the article. In still other embodiments, the antifouling composition including a polymer, where the polymer includes a first monomer represented by Formula I, is applied as a surface coat which is polymerized on the surface of the article.

In some embodiments, the article in the methods or applications is made of materials that include steel, concrete, or a polymer such as, for example, fiberglass.

In some embodiments, the aqueous environment includes salt water. In some embodiments, the aqueous environment includes fresh water. In some embodiments, the aqueous environment includes a bodily fluid such as blood, urine, or saliva.

In some embodiments, the one or more organisms that are killed or their growth abated, are fungi, bacteria, barnacles, mussels, sponges, algae, seaweed, polychaete worms, or sea squirts. In some embodiments, the one or more organisms produce a biofilm.

The present technology, thus generally described, will be understood more readily by reference to the following Examples, which are provided by way of illustration and are not intended to be limiting of the present technology.

EXAMPLES

Example 1

Synthesis of Acrylic-Dioxaborinane Monomers

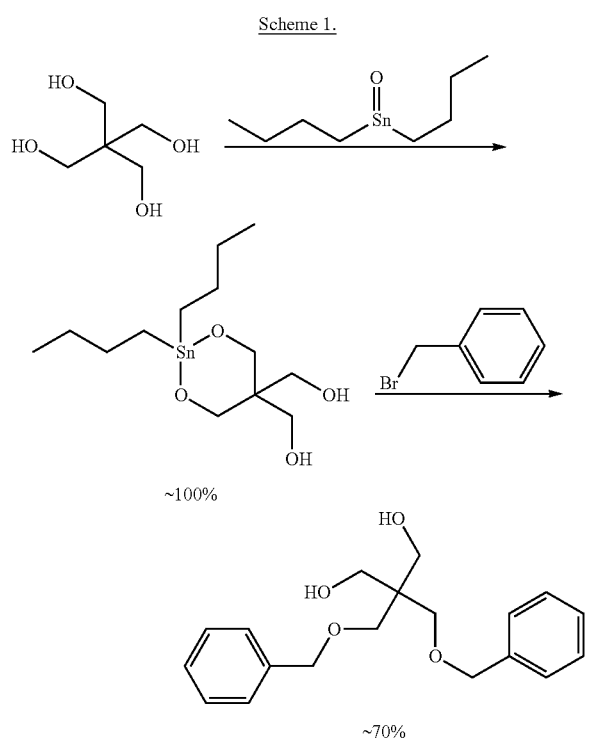

Step 1

Synthesis of bis-esters and ethers of pentaerythritol (Scheme 1)

2,2-Bis(benzyloxymethyl)-1,3-propanediol was prepared by combining pentaerythritol (10.36 g, 100 mmol) and dibutyltin oxide (50.00 g, 200 mmol) under reflux in methanol for four hours. The solvent was then removed by evaporation and the glassy residue was dried by keeping for 1 day at 40° C. under diminished pressure, and then by co-evaporation with toluene. The product was stored in a desiccator.

A suspension of the above stannylene derivative (6.00 g, 10 mmol) in toluene (100 mL) was combined with benzyl bromide (5.00 mL, 40 mmol) and tetraethyl ammonium bromide (270 mg), heated at reflux for four hours, cooled to room temperature, and stirred with water (200 mL). Evaporation of the organic phase gave a residue from which was separated, by chromatography (EtOAc) and recrystallization from petroleum ether, the crystalline dibenzyl ether (70%), mp 73° C., $^1$H NMR: 3.65 (4H); 3.58 (4H); 2.69 (2H); 4.83 (4H); 7.1-7.8 (10H).

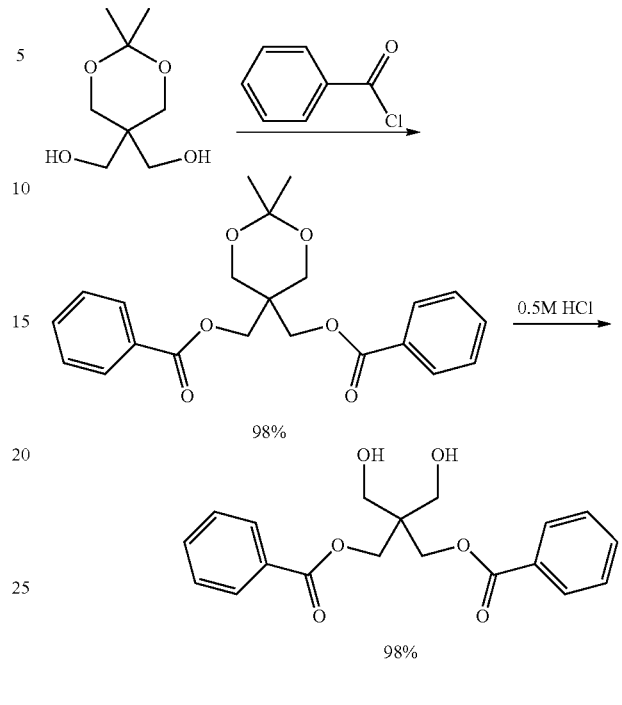

Synthesis of 2,2-bis(benzoyloxymethyl)-1,3-propanediol (Scheme 2)

To an anhydrous THF solution of 2,2-dimethyl-1,3-dioxane-5,5-dimethanol (100 mmol) and $Et_3N$ (340 mmol) at 0° C. was added benzoic acid chloride (220 mmol; 1.1 equiv for each alcohol unit) dropwise over 30 min. The reaction was then allowed to warm to room temperature and was stirred for 15 hours. The crude reaction mixture was evaporated and then extracted from $MeCl_2$ (300 mL) and water (500 mL). The extraction was repeated with 2 portions of $MeCl_2$ (100 mL) followed by drying the combined organic layer over aqueous $Na_2SO_4$, filtering, and evaporating to yield the crude product. The crude benzoic acid, 4-(2,2-dimethyl-1-oxopropyl)-2,2-bis-(hydroxymethyl)-1,3-propanediyl ester, was purified by chromatography (1:1 petroleum ether:EtOAc) in 98% yield. mp 104-105° C.; $^1$H NMR: 2.76 (bs, 2H), 3.79 (s, 4H), 4.52 (s, 4H), 7.6-8.0 (10H).

Step 2

Synthesis of acrylic-dioxaborinane monomers (Scheme 3)

To a three neck flask equipped with a Dean-Stark apparatus and under an inert argon atmosphere was added 13.4 g (78 mmol) of 3-boronic acid propyl methacrylate in toluene (50 mL). To the solution was added 24.7 g (78 mmol) of 2,2-bis (benzyloxymethyl)-1,3-propanediol and the solution was brought to reflux. Water formed from the reaction was collected by the Dean-Stark apparatus, which also served to monitor the progress of the reaction. The reaction typically took four hours to complete. The toluene was then removed by rotary evaporation, which left behind a viscous liquid. The liquid was then purified using EtOAc-hexanes (1:1) and yields were typically 90% or greater.

Scheme 3.

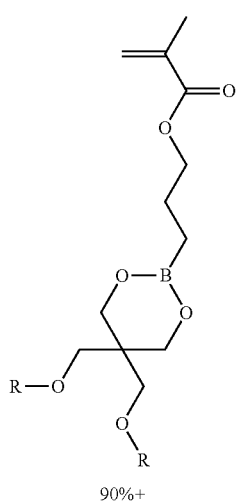

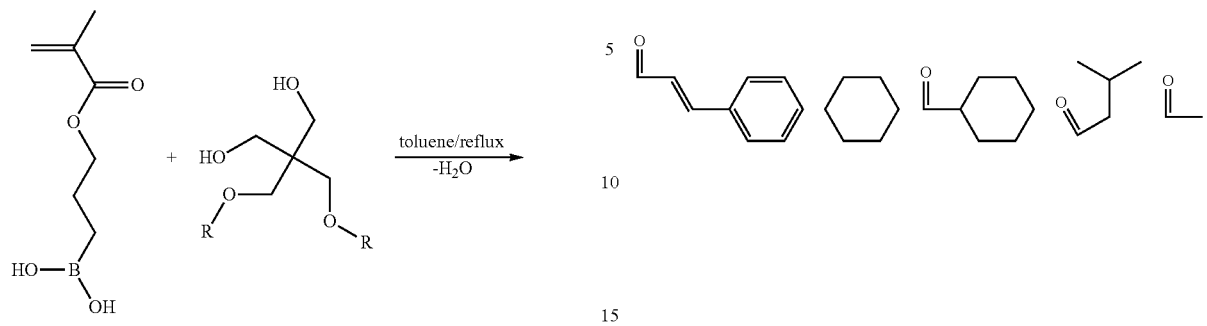

Each of the possible compounds of varying R groups may be prepared by substituting the appropriate diol for the 2,2-bis(benzyloxymethyl)-1,3-propanediol as described for Step 2, above.

Example 2

Synthesis of acrylic-dioxaborinane fatty acid derivative (Scheme 4)

Octadecanoic acid 2-[3-(2-methyl-acryloyloxy)-propyl]-5-octadecanoyloxymethyl-[1,3,2]dioxaborinan-5-ylmethyl ester was synthesized from stearic acid using the procedures outlined above. Dioxaborinane compounds were likewise prepared from other saturated fatty acids, such as lauric and palmitic acid, and unsaturated fatty acids, such as oleic, ricinoleic, linoleic, and linolenic acid.

Scheme 4.

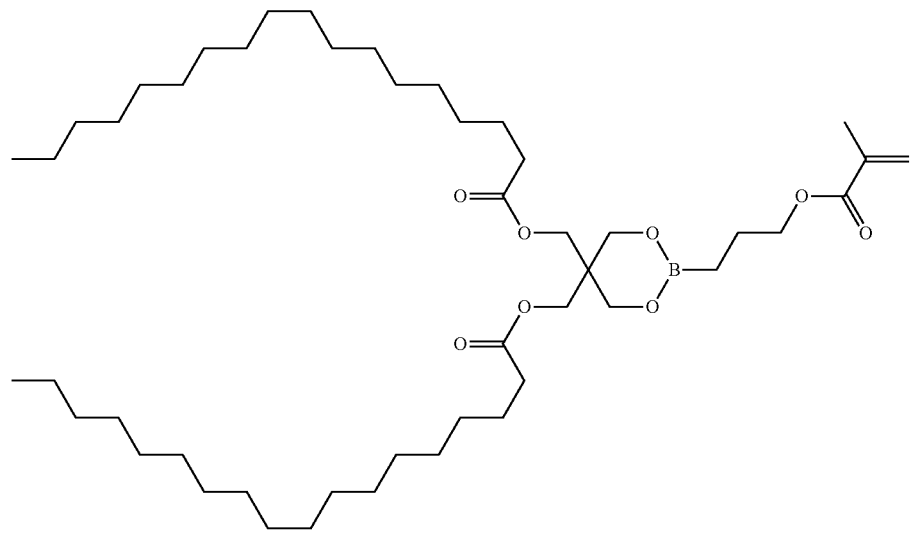

Example 3

Treatment and Polymerization

The hull of a 12-foot fiberglass sailboat is coated with a composition that includes the acrylic acrylic-dioxaborinane monomer shown in Scheme 5 and an AIBN catalyst (2 mol %). The entire boat is heated to 65-75° C. for two hours, causing the acrylic-dioxaborinane preservative to polymerize into a solid coating on the hull.

Scheme 5.

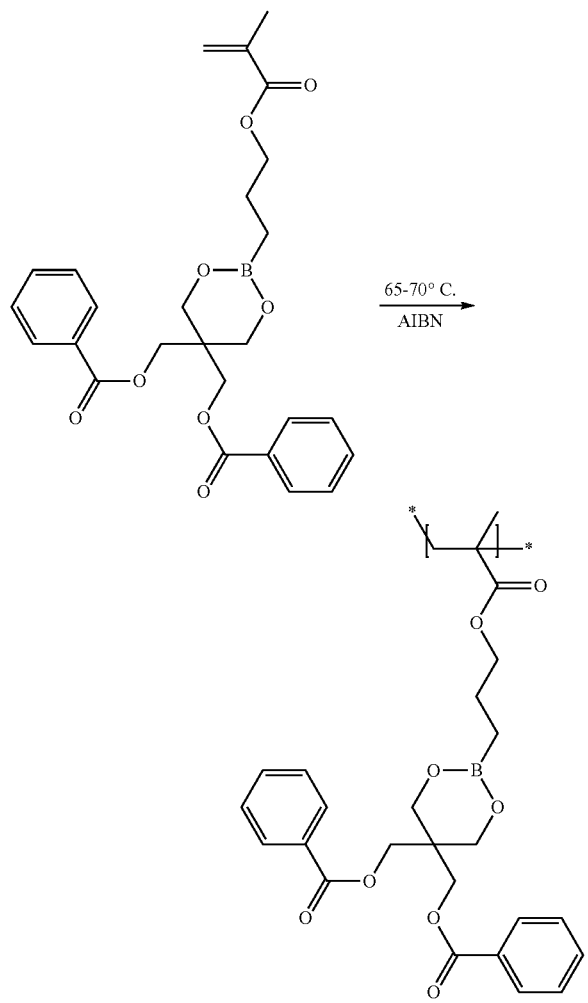

Example 4

Antifouling

The hull of a 12-foot fiberglass sailboat A is untreated. The hull of the same model 12-foot fiberglass sailboat B is coated with an acrylic-dioxaborinane polymer as described in Example 3. The hull of the same model 12-foot fiberglass sailboat C is coated with a copper-based antifoulant. All three sailboats A, B, and C, are to be placed in a natural, salt water environment, e.g., the ocean or bay. The mass of biofilm on each hull, per square centimeter, is then to be measured every thirty days for six months. The hull of sailboat A is expected to accumulate more biofilm than the hulls of sailboats B and C. The hulls of sailboats B and C are expected to accumulate relatively little biofilm.

Example 5

Antifouling: Long-Lasting Formulations

The hull of a 12-foot fiberglass sailboat A is untreated. The hull of an additional fiberglass sailboat C is coated with a copper-based antifoulant, the hull of another sailboat D is coated with an acrylic-dioxaborinane polymer as described in Example 3 and further comprising 2 wt % of silicone rubber binder, and the hull of still another sailboat E is coated with an acrylic-dioxaborinane polymer as described in Example 3 and further comprising 2 wt % of silicone rubber binder and 2 wt % of hydroxyphenylbenzotriazole UV-absorber (stabilizer). All four sailboats A, C, D, and E, are placed into a natural, salt water environment. The mass of biofilm on each hull, per square centimeter, is to be measured every thirty days for six months. The hull of sailboat A is expected to accumulate more biofilm than the hulls of sailboats C, D, and E. The polymer coatings on the hulls of sailboats D and E are expected to persist longer than the coating on sailboat C. Further, the color of the hull of sailboat E is expected to exhibit less fading than the color of the hulls of sailboats A, C, and D.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. An antifouling composition comprising:
a first monomer represented by Formula IA:

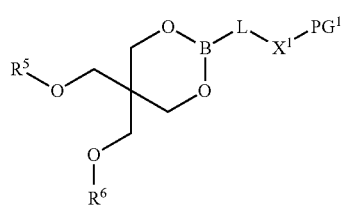

IA wherein:
L is absent, alkylenyl, alkenylenyl, or arylene, wherein the alkylenyl and alkenylenyl are optionally interrupted with one or more oxygen or sulfur atoms;
$X^1$ is absent, amino, oxo, thio, or phosphino;
$PG^1$ is an acrylyl, methacrylyl, epoxyl, isocycanyl, styrenyl, oxyvinyl, thiovinyl, ketovinyl, ketoalkyl, ketoalkoxy, ketoaryl, or cycloalkenyl;
$R^5$ and $R^6$ are independently H, alkyl, alkenyl, aryl, or —C(O)$R^7$;
$R^7$ is alkyl, alkenyl, or aryl; and
wherein: the composition further comprises a carrier, resin, stabilizer, corrosion inhibitor, or a combination of any two or more thereof.

2. The antifouling composition of claim 1, wherein $PG^1$ is C(O)C($R^{10}$)=CH$_2$, C(O)CH=CH$_2$, O—CH=CH$_2$, S—CH=CH$_2$, N=C=O,

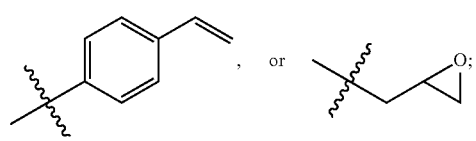

and $R^{10}$ is a $C_1$-$C_8$ alkyl.

3. The antifouling composition of claim 1, wherein $PG^1$ is C(O)C($R^{10}$)=CH$_2$; and $R^{10}$ is H, $C_1$-$C_8$ alkyl, aryl, or CN.

4. The antifouling composition of claim 3, wherein $PG^1$ is C(O)CH=CH$_2$.

5. The antifouling composition of claim 1, wherein $X^1$ is NH, O, S, or PH.

6. The antifouling composition of claim 1, wherein L is $C_1$-$C_{10}$ alkylenyl or arylene, wherein the $C_1$-$C_{10}$ alkylenyl is optionally interrupted with one or more oxygen or sulfur atoms.

7. The antifouling composition of claim 1, wherein $R^5$ is —C(O)alkyl and $R^6$ is C(O)alkyl.

8. The antifouling composition of claim 1, wherein L is $C_1$-$C_{10}$ alkyl.

9. The antifouling composition of claim 1, wherein $X^1$ is O.

10. The antifouling composition of claim 1, further comprising a polymerization product of the first monomer represented by Formula IA, and a second monomer, wherein the second monomer comprises a polymerizable group $PG^2$, which is configured to polymerize with $PG^1$.

11. The antifouling composition of claim 10, wherein the polymerization product comprises 0.1 wt % to 25 wt % of the first monomer represented by Formula IA.

12. The antifouling composition of claim 10, wherein the second monomer is an acrylate or a methacrylate.

13. The antifouling composition of claim 12, wherein the second monomer is represented by Formula II:

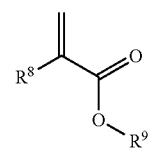

II wherein:
$R^8$ is H; CN; CF$_3$; CH$_3$; or phenyl; and
$R^9$ is H; $C_1$-$C_{22}$ alkyl; aryl; Na$^+$, Li$^+$, or K'.

14. An article coated or impregnated with an antifouling composition, wherein the antifouling composition comprises:
a first monomer represented by Formula IA:

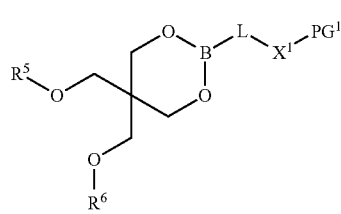

IA wherein:
L is absent, alkylenyl, alkenylenyl, or arylene, wherein the alkylenyl and alkenylenyl are optionally interrupted with one or more oxygen or sulfur atoms;
$X^1$ is absent, amino, oxo, thio, or phosphino;
$PG^1$ is an acrylyl, methacrylyl, epoxyl, isocycanyl, styrenyl, oxyvinyl, thiovinyl, ketovinyl, ketoalkyl, ketoalkoxy, ketoaryl, or cycloalkenyl;

$R^5$ and $R^6$ are independently H, alkyl, alkenyl, aryl, or —C(O)$R^7$;

$R^7$ is alkyl, alkenyl, or aryl; and wherein: the composition further comprises a carrier, resin, stabilizer, corrosion inhibitor, or a combination of any two or more thereof.

15. A method of killing or deterring the growth of one or more organisms on an article, wherein the organisms grow in an aqueous environment, wherein the method includes contacting the article with an antifouling composition comprising:

a first monomer represented by Formula IA:

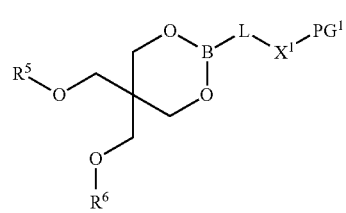

IA wherein:
L is absent, alkylenyl, alkenylenyl, or arylene, wherein the alkylenyl and alkenylenyl are optionally interrupted with one or more oxygen or sulfur atoms;

$X^1$ is absent, or is amino, oxo, thio, or phosphino;

$PG^1$ is an acrylyl, methacrylyl, epoxyl, isocycanyl, styrenyl, oxyvinyl, thiovinyl, ketovinyl, ketoalkyl, ketoalkoxy, ketoaryl, or cycloalkenyl;

$R^5$ and $R^6$ are independently H, alkyl, alkenyl, aryl, or —C(O)$R^7$;

$R^7$ is alkyl, alkenyl, or aryl;

wherein: the composition further comprises a carrier, a resin, a stabilizer, corrosion inhibitor, or a combination of any two or more thereof; and exposing the article to an aqueous environment.

16. The antifouling composition of claim 10, comprising the polymerization product of

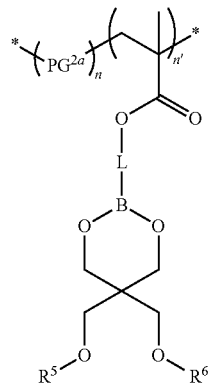

wherein:
$PG^{2a}$ is the polymerized form of the second monomer comprising the polymerization group $PG^2$;

L is an alkylene or arylene group; and n and n' represent the repeat units of the polymerization product.

\* \* \* \* \*